(12) United States Patent
Haas et al.

(10) Patent No.: US 6,770,848 B2
(45) Date of Patent: Aug. 3, 2004

(54) THERMAL WARMING DEVICES

(76) Inventors: William S. Haas, 4615 Durchame Ave., Bartonville, IL (US) 61607; William J. Haas, 1801 Trail Ridge, Flower Mound, TX (US) 75028

( * ) Notice: Subject to any disclaimer, the term of this patent is extended or adjusted under 35 U.S.C. 154(b) by 0 days.

(21) Appl. No.: 10/115,846

(22) Filed: Apr. 3, 2002

(65) Prior Publication Data

US 2002/0153367 A1 Oct. 24, 2002

Related U.S. Application Data

(60) Provisional application No. 60/284,837, filed on Apr. 19, 2001.

(51) Int. Cl.$^7$ ................................................. H05B 3/00
(52) U.S. Cl. ..................... 219/212; 219/217; 219/543; 219/549; 219/527
(58) Field of Search ............................. 219/212, 211, 219/527, 528, 529, 535, 543, 548, 549, 522, 219, 539, 217; 607/96, 108–111; 338/307, 314

(56) References Cited

U.S. PATENT DOCUMENTS

| | | |
|---|---|---|
| 761,250 A | 5/1904 | Porter |
| 2,076,382 A | 4/1937 | Minton |
| 2,342,744 A | 2/1944 | McCready |
| 2,380,346 A | 7/1945 | Thomlinson |
| 2,738,408 A | 3/1956 | Cheviron |
| 2,893,639 A | 7/1959 | Martin |
| 3,164,715 A | 1/1965 | Cotts |
| 3,275,803 A | 9/1966 | True |
| 3,417,229 A | 12/1968 | Shomphe et al. |
| 3,422,244 A | 1/1969 | Lauck, III |
| 3,514,581 A | 5/1970 | Rocholl et al. |
| 3,808,403 A | 4/1974 | Kanaya et al. |
| 3,878,362 A | 4/1975 | Stinger |
| 3,989,924 A | 11/1976 | Kurtzer |
| 4,042,803 A | 8/1977 | Bickford |
| 4,139,763 A | 2/1979 | McMullan et al. |
| 4,198,562 A | 4/1980 | Mills et al. |
| 4,250,398 A | 2/1981 | Ellis et al. |
| 4,270,040 A | 5/1981 | McMullan et al. |
| 4,279,255 A | 7/1981 | Hoffman |
| 4,293,763 A | 10/1981 | McMullan |
| 4,335,725 A | 6/1982 | Geldmacher |
| 4,358,668 A | 11/1982 | McMullan et al. |
| 4,429,215 A | 1/1984 | Sakai et al. |
| 4,507,877 A | 4/1985 | Vaccari et al. |
| 4,626,664 A * | 12/1986 | Grise .......................... 219/543 |
| 4,713,531 A | 12/1987 | Fennekels et al. |
| 4,908,497 A | 3/1990 | Hjortsberg |
| 4,912,306 A * | 3/1990 | Grise et al. .................. 219/543 |
| 5,148,002 A * | 9/1992 | Kuo et al. .................... 219/529 |
| 5,300,101 A | 4/1994 | Augustine et al. |
| 5,300,102 A | 4/1994 | Augustine et al. |
| 5,350,417 A | 9/1994 | Augustine et al. |
| 5,405,371 A | 4/1995 | Augustine et al. |
| 5,714,738 A | 2/1998 | Hauschulz et al. |
| 5,891,189 A | 4/1999 | Payne, Jr. |
| 6,189,487 B1 * | 2/2001 | Owen et al. ................. 219/217 |

OTHER PUBLICATIONS

Japanese Patent No. JP 8106895 & English Abstract; Published Apr. 23, 1996.
French Patent No. FR2769507 & English Abstract; Published Apr. 16, 1996.
French Patent No. FR2577390 & English Abstract; Published Aug. 22, 1986.
German Patent No. DE4140507 & English Abstract; Published Apr. 15, 1993.
French Patent No. FR2041047 & Complete English Translation; Filed Feb. 11, 1970; Published Jan. 21, 1971.

* cited by examiner

Primary Examiner—Tu Ba Hoang

(57) ABSTRACT

A temperature control device comprising a heater element and a power source. The heater element having a conductive ink affixed to a substrate. The power source connected to the conductive ink to supply power to said conductive ink, thereby heating the heater element.

14 Claims, 7 Drawing Sheets

THERMAL WARMING DEVICES

This is a non-provisional application of provisional patent application Ser. No. 60/284,837 filed Apr. 19, 2001.

FIELD OF THE INVENTION

This invention relates generally to temperature control devices, more particularly a temperature control device in a disposable covering for medical applications and as an insert worn under existing clothing.

BACKGROUND OF THE INVENTION

Peri-operative or peri-trauma hypothermia can have serious side effects for any patient. Negative effects include a decrease in cardiovascular stability, an increase in oxygen consumption, and a decrease in resistance to infection. The benefits of maintaining normothermia are well documented. Four recent publications are as follows:

Frank, S. M. et al.; Perioperative Maintenance of Normothermia Reduces the Incidence of Morbid Cardiac Events. *JAMA*, 14:277, 11271–1134, April, 1997.

Cheney, F. W.; Should Normothermia be Maintained During Major Surgery? *JAMA*, 14:277, 1165–1166, April, 1997.

Kurz, A.; Perioperative Normothermia to Reduce the Incidence of Surgerical-Wound Infection and Shorten Hospitalization. *New England Journal of Medicine*, 19:334, 1209–1213, May 1996.

Sessler, D.; Mild Perioperative Hypothermia. *New England Journal of Medicine*, 24:336, June 1997.

Many methods have been used to warm peri-operative and peri-trauma patients including heat lamps, water mattresses, warmed hospital blankets and warm air blowers. These have been frequently proven to be impractical under usual operating constraints.

A warm air heated blanket system is sold by Augustine Medical, Inc. under the name Bair Hugger™ Patient Warming System. This system is effective but requires large non-portable equipment such as a heavy heater/blower system that in many instances is impractical in confined hospital spaces. Also, this system is not desirable for patients with open wounds because the blower system can circulate germs.

A less common rewarming technique is the use of a water circulating mattress. The equipment is heavy, complex, expensive, and may leak. This large non-portable equipment is unusable by paramedic rescue units or in an emergency room, where they are often most needed.

The most common method of treating hypothermia, heated hospital blankets, requires six or more applications before reaching nanothermia. The small amount of heat retained by a cotton blanket quickly dissipates thereby requiring the patients to warm themselves. Although warm blankets are simple and safe, they are inconvenient and time consuming for the nursing staff because laundering and sanitizing of the cotton blankets is necessary.

Another blanket system, West U.S. Pat. No. 6,078,026, supplies current through wires encapsulated between two thin sheets of plastic film. This film is attached to a non-woven polypropylene base fabric by use of stitching or adhesives. The temperature is regulated and provides a method of maintaining a constant temperature. However, this system is heavy, many of the components are expensive and disposed after one use, and the system to conduct current through use of wires between plastic film is disadvantageous because the film-wire combination needs to be affixed to the blanket through either adhesives or stitching. This system is costly and improbable to produce blankets of varied sizes and configurations.

SUMMARY

It is desirable to provide a system for warming patients which overcomes one or more of the above described disadvantages.

It is an object of this invention to provide a reusable, thermal warming device for use in hospitals, and in emergency situations, as well as within clothing.

Another object of this invention is the ability to quickly place the thermal warming device within a disposable covering for use in hospitals and in emergencies.

Another object of this invention is to produce heating elements of varied sizes and configurations.

Another object of this invention is to make reusable the heater element of the thermal warming device.

Another object of this invention to provide a portable direct current power source to be connected to the thermal warming device.

Another object of this invention is to use reusable component parts of a temperature regulating unit and of a power supply source.

Another object of this invention is to make use of a cost effective and efficient means to insert the heater element into blankets and under existing articles of clothing without use of adhesives or stitching.

Another object of this invention is to provide an environmentally friendly method of affixing circuitry to a blanket and to clothing.

Another object of this invention is to quickly heat the element.

Another object of this invention is to provide an safe and efficient method of heating a body or surface.

These, and other objects and advantages of the present invention, will become apparent as the same becomes better understood from the Detailed Description when taken in conjunction with the accompanying drawings.

DETAILED DESCRIPTION

Figure 1:
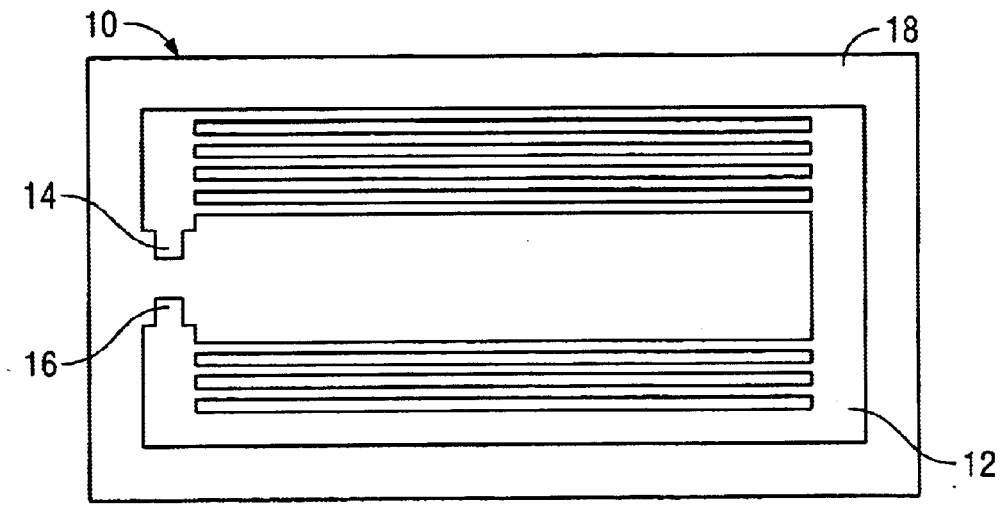
FIG. 1. illustrates the heater element 10.

Reference is now made more particularly to the drawings which illustrate the best presently known mode of carrying out the invention and wherein similar reference characters indicate the same parts throughout the several views. FIG. 1 shows a heater element 10. The heater element 10 includes conductive ink 12 and substrate 18.

In the preferred embodiment, the conductive ink 12 includes a first conductive ink pad 14 and a second conductive ink pad 16 as shown in FIG. 1. The conductive ink 12 is constructed of UV ink, made be Allied PhotoChemical, Kimball, Mich. The preferred conductive ink 12 is FD 3500 CL UV ink, which is 100% UV (ultra violet) curable. Other materials including conductive foils and woven fabrics that conduct heat are suitable alternatives to the conductive ink. The UV ink is light curable by the process called photopolymerization. The UV ink provides flexible circuitry, ideally suited for use as a conductive ink 12.

Circuitry is printed onto the substrate 18 of the preferred embodiment using a conventional printing press or a screen printing press. The process for affixing the conductive ink 12 to the substrate 18 to construct the heater element 10 begins with a pattern of lines drawn using a computer and a computer aided drawing program. The final drawing information is then used to generate a film positive, which is transferred to a screen, stencil material, or printing plate. The screen, stencil material, or printing plate is used to apply the conductive ink 12 to a substrate 18; the preferred substrate being a clear Mylar®, 3 to 5 mil thickness. An alternative substrate 18 is Liquiflex® 50C-104 grade 05379 (Plain) protective packaging film made by Curwood®, Oshkosh, Wis.

Figure 5A:
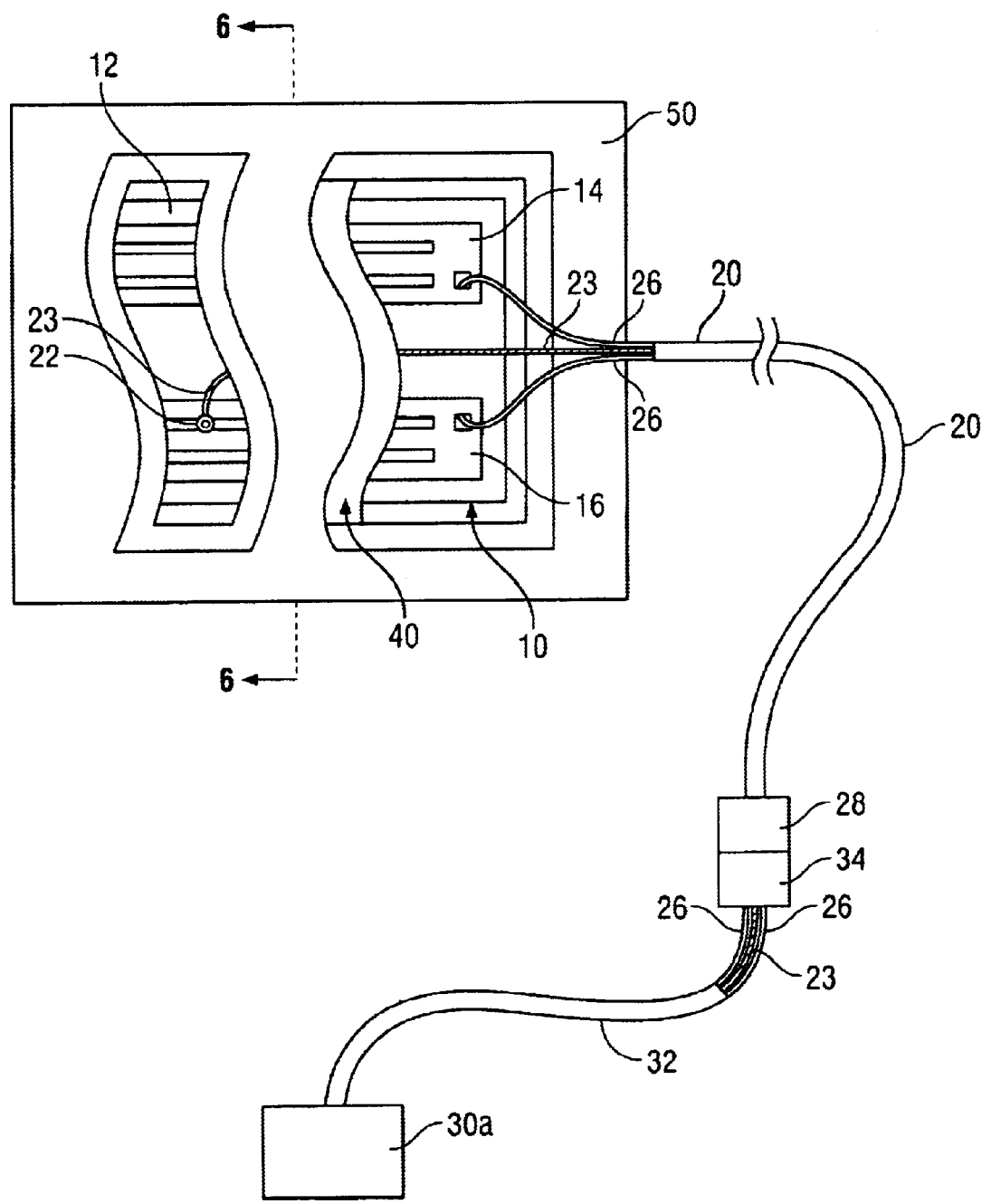
FIG. 5*a* illustrates the preferred temperature controller 30. Also shown is the heater element 10 placed inside the pouch 40 which is in turn placed inside blanket 50.
Figure 5B:
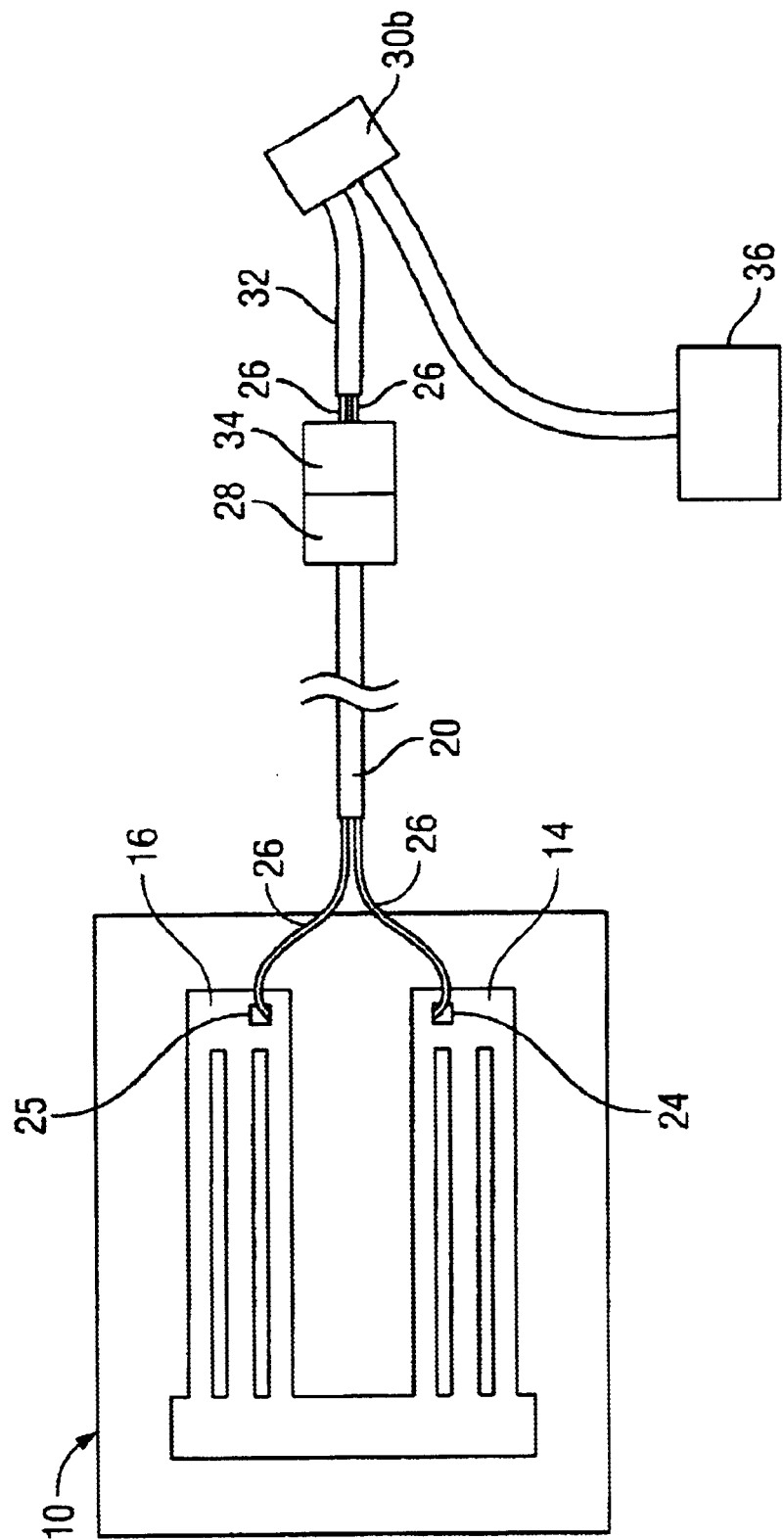
FIG. 5*b* illustrates the heater element 10 connected to the alternate temperature controller 30.
Figure 5C:
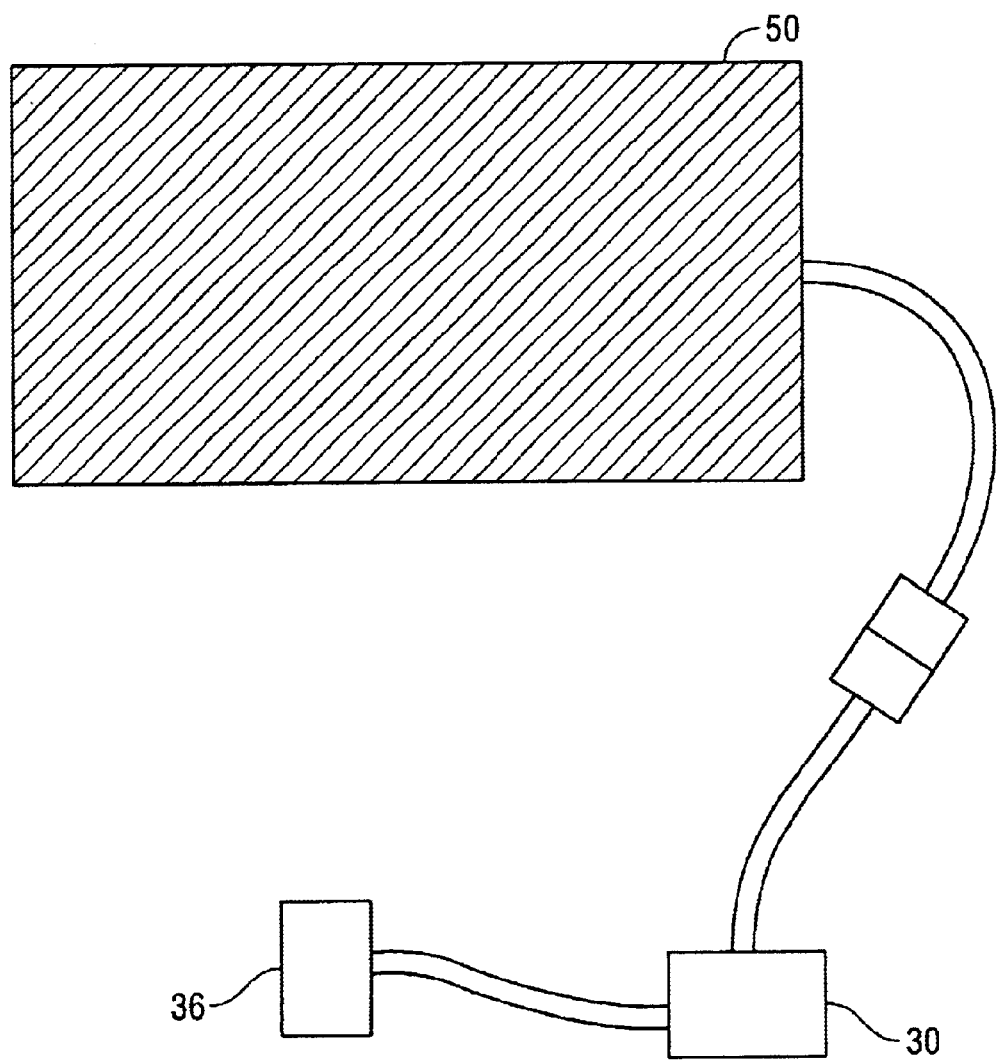
FIG. 5*c* illustrates blanket 50 and alternate temperature controller 30 connected to power source 36.

The application of the conductive ink 12 can be done by hand 4, or automatically, by using a printing press. Once the conductive ink 12 is applied to the substrate 18, UV (ultra violet) light is introduced to cure, set, and harden the conductive ink 12. Once the conductive ink 12 is cured to the substrate 18, the heater element 10 is ready to be connected to a temperature controller 30, as shown in FIGS. 5a, 5b & 5c and to heat the heater element 10. The heater element 10 also may be reusable when placed within a hygienic barrier or pouch. The heater element 10 may be placed within other articles of clothing, such as gloves and shoes, was well as within sleeping bags and sports seats. In an alternative embodiment, the substrate 18 may be a mirror, glass, window, or any other solid surface that needs to be heated.

Figure 2:
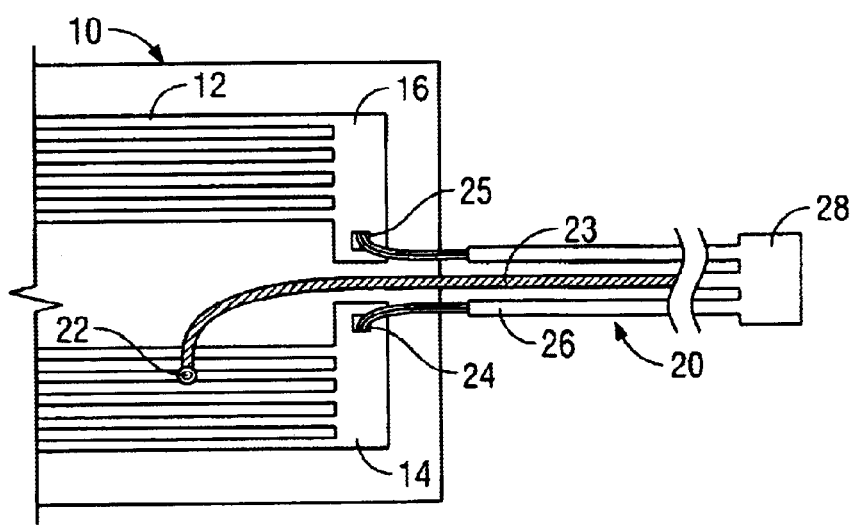
FIG. 2 illustrates the heater element 10 connected to the temperature connector 20.
Figure 3:
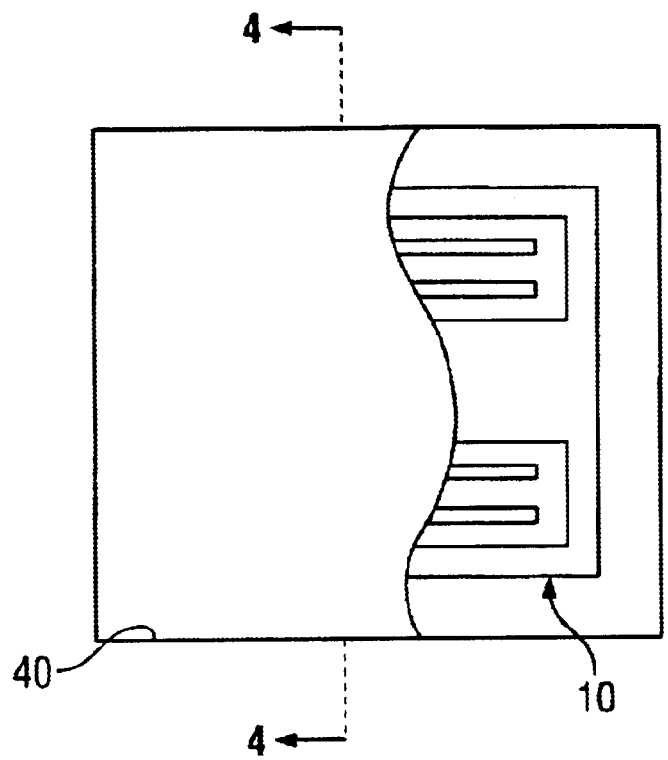
FIG. 3 illustrates the heater element 10 placed within the pouch 40.

Once the heater element 10 is constructed, a temperature connector 20 is attached to the conductive ink 12 of the heater element 10, as shown in FIG. 2. The temperature connector will be later shown to connect the heater element 10 to a power source 36. It is the preferred embodiment that the heater element 10, with the temperature connector 20 attached, is placed within a pouch 40, as shown in FIG. 3. The pouch 40 is then hermetically sealed. In the preferred embodiment, where the heater element 10 is placed within the pouch 40, the heater element 10 and pouch 40 may be disposable. This allows for reuse of the heater element 10 and the pouch 40.

Figure 4:
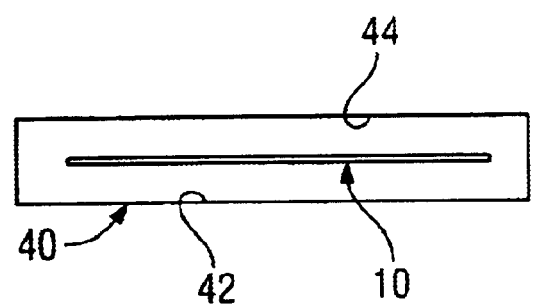
FIG. 4 represents a cutaway along line 4—4 in FIG. 3.

The pouch 40 has a first side 42 and a second side 44 and a space between the first side 42 and a second side 44, as shown in FIG. 4. This allows for the heater element 10 to be inserted into the space between the first side 42 and second side 44. The pouch 40 is constructed of Liquiflex® 50C-104 grade 05379 (Plain) protective packaging film made by Curwood®, Oshkosh, Wis. The material used to construct the pouch 40 pouch 40 be covered by disposable material or one with reusable qualities, such as blanket 50 or article of clothing 60a, 60b, 60c.

Figure 7:
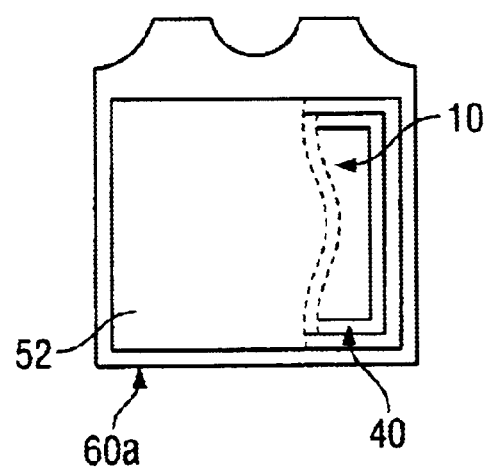
FIG. 7 represents a view of the article of clothing 60*a*, in the form of a vest, where heater element 10 is placed within pocket 52 of article of clothing 60*a*.
Figure 8:
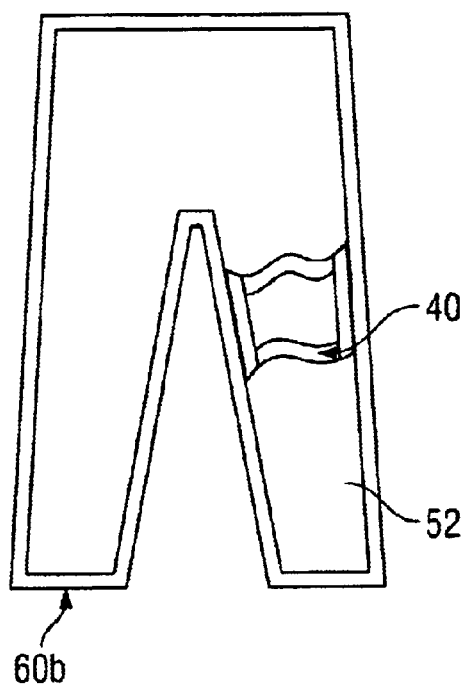
FIG. 8 represents a view of the article of clothing 60*b*, in the form of pants, where heater element 10 is placed within pocket 52 of article of clothing 60*b*.
Figure 9:
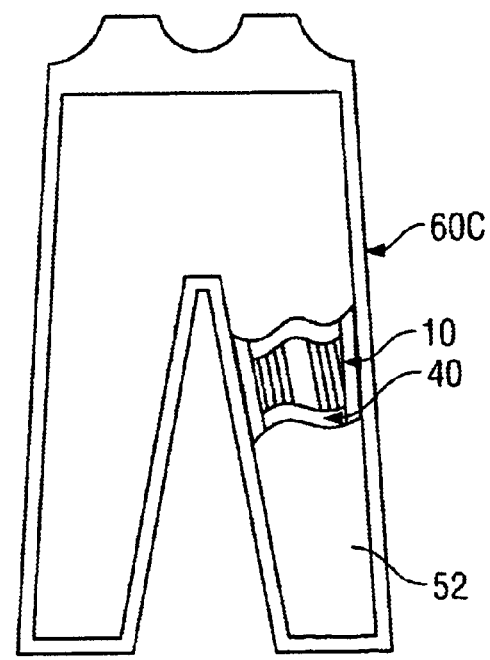
FIG. 9 represents a view of the article of clothing 60c, in the form of coveralls, where heater element 10 is placed within pocket 52 of article of clothing 60c.

The user may dispose of the pouch 40 and reuse the heater element 10 by unsealing the pouch 40, removing the heater element 10 and placing the heater element 10 within a new pouch 40. Once the heater element is sealed within the pouch 40, the pouch 40 may be placed inside a pocket 52 within a blanket 50, as shown in FIG. 5a. Alternatively, pouch 40 can be placed inside a pocket 52 within an article of clothing 60a, 60b, or 60c, as shown in FIGS. 7, 8, and 9. In yet another embodiment, the heater element 10 can be affixed directly to a blanket 50 or affixed directly to an article of clothing 60a, 60b, 60c.

The heater element 10 may be sized to accompany adult or infant sized blankets, as well as sized to accompany varied sizes and configurations for personal use. Additionally, blanket 50 is sized according to the desired use, whether for use as wrap around a human body, or sized according to dimensions of clothing. The blanket 50 is constructed of a material which is non-woven polypropylene base fabric such as is employed in disposable surgical drapes and gowns. The preferred material is Spunbond/Meltblown/Spunbond (SMS) fabric. This SMS fabric is made by Kimberly-Clark, Boswell, Ga. Other material may be used, but any alternate material must meet the flammability requirements of the Nation Fire Protection Association Standard NFPA 702-1980.

Additionally, article of clothing 60a, 60b, 60c is sized according to the desired use: whether as use as an article of clothing 60a designed to cover the body of a human patient; whether as use as an article of clothing 60b designed to cover the legs of a human patient; or as an article of clothing 60c designed to cover the entire person of a human patient. The article of clothing 60a, 60b, 60c is constructed of a non-flammable fabric. Any suitable fabric may be used, however the fabric must meet the flammability requirements of the Nation Fire Protection Association Standard NFPA 702-1980, and be able to be laundered.

Figure 6:
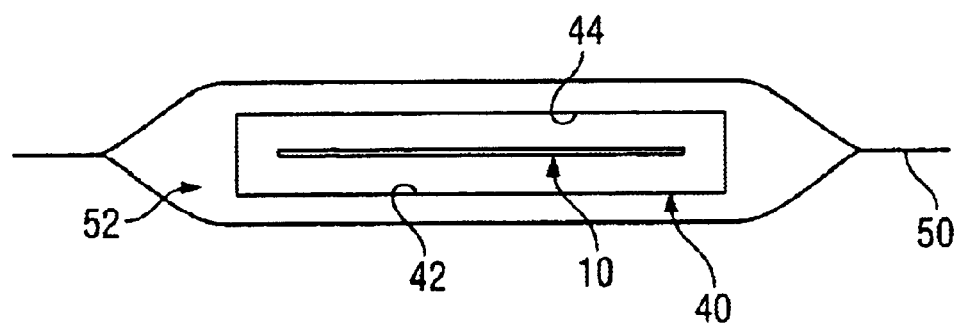
FIG. 6 illustrates a cutaway along line 6—6 in FIG. 5*a* showing the pouch 40 placed inside pocket 52 of blanket 50.

In the preferred embodiment, the pouch 40 placed within a pocket 52 which is within the blanket 50, as shown in FIG. 5a, or placed inside a pocket 52 incorporated within article of clothing 60a, 60b, 60c, as shown in FIGS. 7, 8, and 9. This allows for the heater element 10 to be reused. Alternatively, the pouch 40 may be placed directly onto a human patient. In addition, the pouch 40 may be placed within a blanket 50 or within an article of clothing 60a, 60b, 60c. The pouch 40 may be affixed to the blanket 50 as follows: by placing the pouch 40 in a pocket 52 within blanket 50, or stitching the pouch 40 to the blanket 50, or by using adhesive to attach the pouch 40 to the blanket 50. Alternatively, the pouch 40 may be affixed to article of clothing 60a, 60b, 60c in the same manner the pouch 40 is affixed to blanket 50, and the heater element 10 is placed within the pouch 40 (as shown in FIGS. 6, 7 and 8).

A power source 36 connects to the conductive ink 12 to supply power for heating the heater element 10 to approximately +100 degrees Fahrenheit. In the preferred embodiment, the power source 36 is contained within a temperature controller 30. The temperature controller 30 regulates the power source 36 by controlling the amount of current supplied to the conductive ink 12 and thereby regulating the temperature of the heater element 10. The temperature controller 30 containing the power source 36 connects to the conductive ink 12 via a temperature cable 32, as shown in FIG. 5a. The temperature cable 32 connects to the temperature connector 20, as shown in FIG. 5a. The temperature connector 20 connects to the conductive ink 12, as shown in FIG. 5a.

The power source 36 may be DC, AC, solar power, or any other source that may be converted into direct current power and supplied to the conductive ink 12. In the preferred embodiment, the power source 36 is either a single or dual Ni-MH battery pack, made by AVT, Inc, and contained within the temperature controller 30. Each individual pack consists of twelve +1.2 volt cells in series to yield an overall voltage of +14.4 VDC rated at 6.8 amp-hours. The combined capacity of both battery packs yields 14–16 hours of use or 8–10 hours with a single battery pack.

In the preferred embodiment, the power source 36, which is in the form of battery packs, is charged by a battery charger, preferably a Texas Instruments, Inc. Model DV2005S1 Series. The battery charger receives its power from a boost converter that steps up the volt output of the internal power supply. This higher voltage is required in order to properly charge the twelve cell battery pack. The battery charger also incorporates safety features that will terminate the charge cycle if the battery temperature, maximum charge time and maximum voltage exceeds set limits.

The capacity of the power source 36 is determined by measuring the voltage and displaying the results visually through use of a capacity meter, made by WJH Engineering part number 58-90001000-000. The capacity meter utilizes a National Semiconductor device (LM3419) that is designed to drive a series of five LEDs indicating FULL, ¾, ½, ¼ or EMPTY battery. When the capacity of the power source 36 drops below the minimum set threshold an alarm sounds. The capacity meter is electrically removed from operation when the temperature controller 30 turns off the power source 36, this keeps the battery packs from self-discharging.

The power source 36 may alternatively be an AC source, the temperature controller 30 contains a switching power supply that is capable of operating from 85 to 250 VAC at a rated output of 15VDC @ 7 amps. The switching power supply also provides the power to charge the internal battery pack(s). The power source 36 may alternatively be a DC source, the temperature controller 30 may operate from +12 to +16 VDC source such as a vehicle cigarette lighter or from a DC source within an emergency vehicle.

The temperature controller 30 is a device that is preferably used to accurately control the temperature of the heater element 10 to +100 +/–4 degrees Fahrenheit. Alternatively, the temperature controller 30 may regulate the temperature of the blanket 50 or article of clothing 60a, 60b, and 60c. The temperature controller 30 consists of the following major components.

The temperature controller 30 includes a proportional integral derivative (PID) controller, made by Oven Industries part number 5C7-362, that is capable of operating in P, PI, PD or PID control. The PID controller is capable of allowing the heater element 10 to be heated to +100 degrees Fahrenheit within 2 minutes. After the first heating of the heater element 10, subsequent heatings of the heater element 10 occur much more quickly. This PID controller is programmable via an RS232 communication port for direct interface with a compatible PC. The RS 232 communications interface has 1500 VAC isolation from all other electronic circuitry minimizing interferences from noise or errant signals caused by common ground loops. This controller will accept a communications cable length in accordance with RS232 interface specifications. Once the desired set parameters are established, the PC may be disconnected and all parameter settings are retained in non-volatile memory. The output signal to the heater element 10 is Pulse Width Modulated and is PC selectable for either 675 Hz or 2700 Hz operation. Pulse Width Modulation averages the amount of energy provided to the heater element 10 and reduces the extreme temperature excursions experienced with an "on/off" system. This tends to extend the life and reliability of the battery source. The PWM control scheme affords control accuracy to within +/–0.05° C. at the control sensor.

The preferred temperature controller 30 utilizes a thermistor 22, as shown in FIG. 5a. The thermistor 22, or control sensor, for the temperature controller 30 is a Negative Temperature Coefficient (NTC) Thermistor, made by Panasonic, Inc. part number ERT-D2FHL153S, rated at 15,000 ohms at +25° C. In order to provide accurate control of the temperature at the patient location, it is preferred that the thermistor 22 be affixed to the heater element 10. Alternatively, the thermistor 22 may be attached to the blanket 50 or located within articles of clothing 60a, 60b, 60c.

The temperature controller 30 incorporates several safety devices to protect the patient from potential injury. If the temperature of the heater element 10 reaches above +104° F. the temperature controller 30 automatically shuts off the power to the heater element 10 and sounds an alarm, made by International Component part number BRP2212L-12-C. The alarm can be programmed to any upper limit and can be reset by the temperature controller 30. The temperature controller 30 can also indicate visually when the temperature of the heater element 10 falls below +98° F. or when the temperature is within a programmable target window. The temperature controller 30 will also sound an alarm if the temperature cable 32 becomes disconnected from the temperature connector 20 or if the thermistor 22 is at fault and becomes shorted or opened.

There are two embodiments for connecting the heater element 10 to the temperature controller 30 and controlling the temperature of the heater element 10. The first is used in various medical applications where the temperature of the heater element 10 must be extremely controlled and regulated within +100+/–4° F. This embodiment will be referred to as the preferred temperature controller 30. The other embodiment is intended for individual use where the user controls the temperature of the heater element 10 directly and can vary the temperature between +100 and +110° F. This embodiment will be referred to as the alternate temperature controller 30.

The preferred temperature controller 30, as depicted in FIG. 5a, regulates the temperature of the heater element 10. The preferred temperature controller 30 has a temperature cable 32 which contacts the heater element 10 via a temperature connector 20. The temperature connector 20 attaches to the heater element 10. In the preferred temperature controller embodiment, the temperature connector 20 comprises heater element wires 26, a thermistor 22, thermistor wires 23, a first heater element contact pad 24, a second heater element contact pad 25, and a first socket 28, as shown in FIG. 2. The heater element wires 26 are 18 gauge wire. The heater element wire 26 contacts the first heater element contact pad 24 and second heater element contact pad 25. The contact pads 24 and 25 are constructed of copper squares, or may be constructed of other conductive material. In turn, the first heater element contact pad 24 contacts the first conductive ink pad 14 and the second heater element contact pad 25 contacts the second conductive ink pad 16. Adhesive tape is used to affix the heater element contact pads to the conductive ink pads.

Thermistor wires 23 are soldered to a thermistor 22. Adhesive tape is used to affix the thermistor 22 to the heater element 10. Once the temperature connector 20 is affixed to the heater element 10, the temperature connector 20 may be attached to the temperature cable 32, as shown in FIG. 5a. In this embodiment, the temperature cable 32 contains a second socket 34 and four wires, two of the wires are heater element wires 26 and the two other wires are thermistor wires 23. When the first socket 28 is affixed to the second socket 34, the temperature connector 20 connects to the temperature cable 32. Thus, the power source 36 is connected to the conductive ink 12 and current is allowed to be supplied from the power source 36 to the conductive ink 12 via heater element wires 26. In addition, the preferred temperature controller 30 connects to the thermistor 22 via thermistor wires 23. The preferred temperature controller 30 also controls the power source 36 by regulating the amount of power supplied to the conductive ink 12, similar to the temperature controller 30 as discussed above.

The alternate temperature controller 30, as shown in FIG. 5b, comprises a similar configuration as the preferred temperature controller 30, however it does not encompass a thermistor 22 and thermistor wires 23. An additional difference is that the heater element wires 26 are 22 gauge wire.

The alternate temperature controller 30 does not utilize a thermistor as a feedback for controlling the temperature of the element like the preferred temperature controller 30 does. Instead the user controls the temperature of the heater element 10 by sensing the warmth of the heater element 10 and adjusts a control knob within the alternate temperature controller 30 to achieve the desired comfort. The alternate temperature controller 30 thereby regulates the amount of power supplied by the power source 36 to the conductive ink 12. The alternate temperature controller 30 consists of a solid state switch (MOSFET), an a stable timer (NE555), a voltage comparator (LM393), a battery connector, a heating element connector and a control potentiometer with a built in On/Off switch.

The basic design principle is to turn the solid state switch on and off very quickly and vary the current output supplied to the conductive ink 12 by changing the ratio of the "On" time to "Off" time. The ratio is adjustable from 0% (completely turned off) to 100% (completely turned on) by using the control potentiometer to vary the input to the voltage comparator. The variable input voltage is then compared against the output voltage of the timer. Every time the voltage output of the timer crosses the threshold of the compatator the output of the controller turns on and then back off. The frequency of this On/Off cycle is selected to be approximately 300 Hz.

In the alternate temperature controller 30 embodiment, the alternate temperature controller 30 controls a power source 36, which is in the form of a battery, preferably a nickel metal hydride type rechargeable battery, made by AVT, Inc. Also, a battery charger, preferably a XENOTRONIX, Inc.™ Model MHTX-7 Series, is used to recharge the battery. Alternatively, in the alternate temperature controller 30, the power source 36 may be a DC source when it is available. The alternate temperature controller 30 is capable of operating from +12 to +16 VDC source such as a vehicle cigarette lighter or from a DC source within an emergency vehicle.

The preferred way of connecting the temperature controller 30 containing the power source 36 to the conductive ink 12 and controlling the temperature of the heater element 10 is shown in FIG. 5a. The conductive ink 12 contacts the temperature connector 20 via the first conductive ink pad 14 and second conductive ink pad 16. The temperature connector 20 then is attached to the temperature cable 32 via the first socket 28 and the second socket 34. The temperature cable 32 is attached to the temperature controller containing the power source 36. The preferred temperature controller 30 connects to the thermistor 23 and to the power source 36. The heater element 10, with the temperature connector 20 attached, is then placed within a pouch 40 and hermetically sealed. Once the user activates the temperature controller 30, current is supplied from the power source 36 to the heater element 10 and the temperature controller 30 in connection with the thermistor 23 regulates the temperature of the heater element 10. The pouch 40 can then be placed within a pocket 52 of a blanket 50, or alternatively the pouch 40 may be placed within a pocket 52 within article of clothing 60a, 60b, 60c.

It is now deemed apparent that there has been described an improvement in a thermal warming device. The heater element 10, pouch 40, temperature controller 30 and temperature connector 20 may be disposable. Additionally, the heater element 10 is heated quickly. While a preferred embodiment of the invention has herein been illustrated and described, this has been done by way of illustration and not limitation, and the invention should not be limited except as required by the scope of the appended.

I claim:

1. A blanket comprising a pocket defining a substantially enclosed pocket space;

a substrate having upper and lower sides;

a heating matrix associated with the substrate, the heating matrix including a circuit printed on at least one side of the substrate;

a pouch defining a substantially enclosed pouch space receiving the substrate with the heating matrix thereon;

the pouch being removably received in the pocket space; and means for connecting the heating matrix to a power source.

2. A blanket as set forth claim 1, wherein the pouch is made of a sheet of a non-flammable material.

3. A blanket as set forth in claim 2, wherein the non-flammable material is a non-woven polypropylene fabric.

4. A blanket as set forth in claim 1, wherein the power source is a direct current power source.

5. A blanket as set forth in claim 4, wherein the direct current power source is comprised of a rechargeable battery.

6. A blanket as set forth in claim 4, including an AC/DC converter to allow a standard 110 V AC wall outlet to act as the power source.

7. A blanket as set forth in claim 1, wherein the means for connecting the power source with the heating matrix includes a power cord with a first end attached to the substrate, said first end being electrically connected with the heating matrix, and a second end detachably connected with the power source.

8. A blanket as set forth in claim 7, wherein the first end of the power cord is attached to the substrate by an adhesive.

9. A blanket as set forth in claim 1, wherein the means for connecting the power source with the heating matrix includes a plug attached to the substrate, said plug being electrically connected with the heating matrix and a power cord with first and second ends and with a receptacle at the first end designed to accept the plug and detachably connected at the second end with the power source.

10. A blanket as set forth in claim 9, wherein the plug is attached to the substrate by an adhesive.

11. A blanket as set forth in claim 9, wherein the second end of the power cord is provided with a second plug suitable for insertion into a cigarette lighter receptacle, allowing the cigarette lighter receptacle to function as the power source.

12. A blanket as set faith in claim 1, further comprising means for controlling the temperature of the heating matrix including a temperature sensing means in communication with the hearing matrix and a temperature controller connected with the temperature sensing means.

13. A blanket comprising a substrate of polyethylene film having upper and lower sides; a heating matrix associated with the polyethylene film, the heating matrix having a heating circuit printed on at least one side of the substrate of the polyethylene film; a pocket defining a substantially enclosed pouch space; a pouch defining a substantially enclosed pouch space receiving the substrate with the heating matrix thereon substrate; the pouch being removably received in the pocket and means for connecting the heating matrix to a power source.

14. A heating article comprising:

a pocket defining a substantially enclosed pocket space;

a substrate having upper and lower sides;

a heating matrix associated with the substrate, the heating matrix including a circuit printed on at least one side of the substrate;

a pouch defining a substantially enclosed pouch space receiving the substrate with the heating matrix thereon; the pouch being removably received in the pocket space;

and means for connecting the heating matrix to a power source.

\* \* \* \* \*